United States Patent
Kojima et al.

(10) Patent No.: US 9,888,887 B2
(45) Date of Patent: Feb. 13, 2018

(54) X-RAY DIAGNOSTIC APPARATUS AND X-RAY DIAPHRAGM THEREOF

(71) Applicant: Toshiba Medical Systems Corporation, Otawara-Shi (JP)

(72) Inventors: Tsuyoshi Kojima, Nasushiobara (JP); Yoshiyuki Sato, Nasushiobara (JP); Katsuaki Shinoda, Shioya (JP); Shinsuke Ooie, Yaita (JP)

(73) Assignee: TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 253 days.

(21) Appl. No.: 14/819,557

(22) Filed: Aug. 6, 2015

(65) Prior Publication Data
US 2016/0051210 A1  Feb. 25, 2016

(30) Foreign Application Priority Data
Aug. 21, 2014 (JP) .................. 2014-168332

(51) Int. Cl.
*G21K 1/04* (2006.01)
*A61B 6/06* (2006.01)
*A61B 6/10* (2006.01)
*A61B 6/00* (2006.01)

(52) U.S. Cl.
CPC .............. *A61B 6/06* (2013.01); *A61B 6/54* (2013.01); *G21K 1/04* (2013.01); *A61B 6/107* (2013.01); *A61B 6/4291* (2013.01); *A61B 6/4441* (2013.01); *A61B 6/542* (2013.01)

(58) Field of Classification Search
CPC ........ A61B 6/4035; A61B 6/107; A61B 6/542; A61B 6/06; A61B 6/54; A61B 6/4291; A61B 6/4441; G21K 1/04
USPC ................................... 378/145–153
See application file for complete search history.

(56) References Cited

U.S. PATENT DOCUMENTS

2015/0245804 A1* 9/2015 Kieft .................. A61B 6/06
378/147

FOREIGN PATENT DOCUMENTS

JP        2005-6971       1/2005

* cited by examiner

*Primary Examiner* — Courtney Thomas
(74) *Attorney, Agent, or Firm* — Oblon, McClelland, Maier & Neustadt, L.L.P.

(57) ABSTRACT

An X-ray diagnostic apparatus according to the present embodiment includes: an X-ray tube which generates X-rays to be irradiated at an object; an X-ray diaphragm which houses an X-ray shielding member forming an irradiation aperture, through which the X-rays pass, along a side surface of the X-ray tube; an X-ray detector which detects X-rays passing through the object; and an image data generation circuitry which generates image data based on the X-rays detected by the X-ray detector.

15 Claims, 12 Drawing Sheets

X-RAY DIAGNOSTIC APPARATUS AND X-RAY DIAPHRAGM THEREOF

CROSS-REFERENCE TO RELATED APPLICATION

This application is based upon and claims the benefit of priority from Japanese Patent Application No. 2014-168332, filed on Aug. 21, 2014, the entire contents of which are incorporated herein by reference.

FIELD

Embodiments as an aspect of the present invention relate to an X-ray diagnostic apparatus and an X-ray diaphragm thereof.

BACKGROUND

Conventionally, an X-ray diagnostic apparatus is known which irradiates radioactive rays such as X-rays at an object, detects the X-rays passing through the object, acquires projection data, and generates image data on the basis of the projection data.

The X-ray diagnostic apparatus includes an X-ray tube capable of firing X-rays, and a movable diaphragm, which limits an irradiation area of X-rays to spare the object from excessive exposure to radiation is disposed on a front surface of the X-ray tube. The movable diaphragm can set an X-ray irradiation field (irradiation area) to a desired region by adjusting an extent of opening of built-in diaphragm blades. To set the X-ray irradiation field, it is necessary to check the irradiation field on the object, and performing this check without actually firing X-rays is important.

Therefore, a movable diaphragm device and a radiographic apparatus have been proposed with which a clear X-ray irradiation field can be obtained as well as radiation conditions required for obtaining the same irradiation result can be relaxed.

In the X-ray diagnostic apparatus having a movable diaphragm, the movable diaphragm typically includes four diaphragm blades, and to set the X-ray irradiation field, the movable diaphragm moves each diaphragm blade in a horizontal direction relative to the X-ray tube so as to open/close an irradiation aperture.

However, since the movable diaphragm has such a structure that all the four diaphragm blades are opened to open the irradiation aperture, it is necessary to clear an area corresponding to the four diaphragm blades when fully opening the irradiation aperture.

In particular, since the movable diaphragm is often used in close contact with the object, securing a retraction space for retracting the diaphragm blades raises a problem that the size of the main body of the movable diaphragm increases.

DETAILED DESCRIPTION

First, a problem with a conventional X-ray diagnostic apparatus having a movable diaphragm will be described with the drawings, which will be followed by a description of an X-ray diagnostic apparatus according to the present embodiment.

Figure 11:
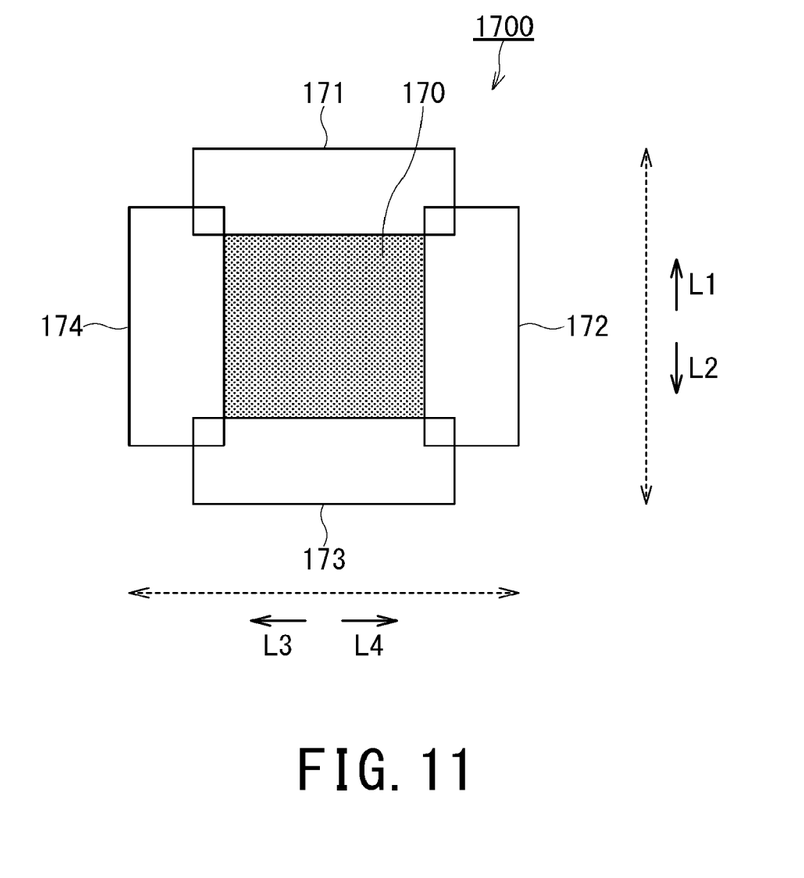
FIG. 11 is a configurational view showing a movable diaphragm in a conventional X-ray diagnostic apparatus.

FIG. 11 is a configurational view showing a movable diaphragm 1700 in the conventional X-ray diagnostic apparatus.

As shown in FIG. 11, the movable diaphragm 1700 of the conventional X-ray diagnostic apparatus is composed of four diaphragm blades 171 to 174. The diaphragm blade 171 and the diaphragm blade 173 make a pair and move in a direction L1 or a direction L2. The diaphragm blade 172 and the diaphragm blade 174 make a pair and move in a direction L3 or a direction L4.

Here, when minimizing an imaging area defined by an irradiation aperture 170, that is, when fully closing the irradiation aperture 170, the four diaphragm blades 171 to 174 each shield the irradiation aperture 170 toward its center (in an inward direction).

When maximizing the imaging area defined by the irradiation aperture 170, that is, when fully opening the irradiation aperture 170, the four diaphragm blades 171 to 174 each retract in an opposite direction (in an outward direction) from the center of the irradiation aperture 170.

Figure 12A:
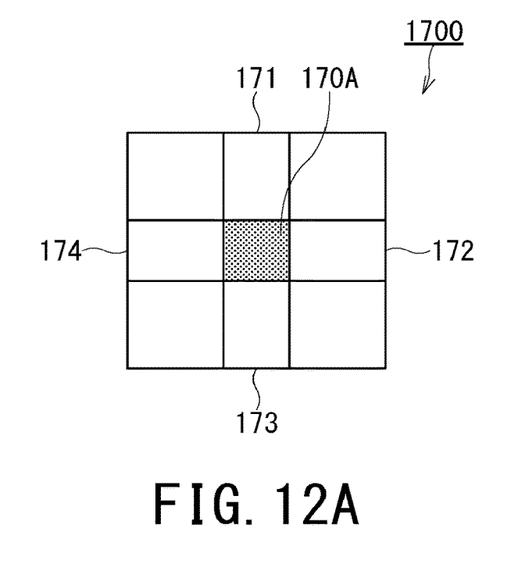
FIG. 12A and FIG. 12B are views illustrating changes in action of four diaphragm blades in the movable diaphragm of the conventional X-ray diagnostic apparatus.
Figure 12B:
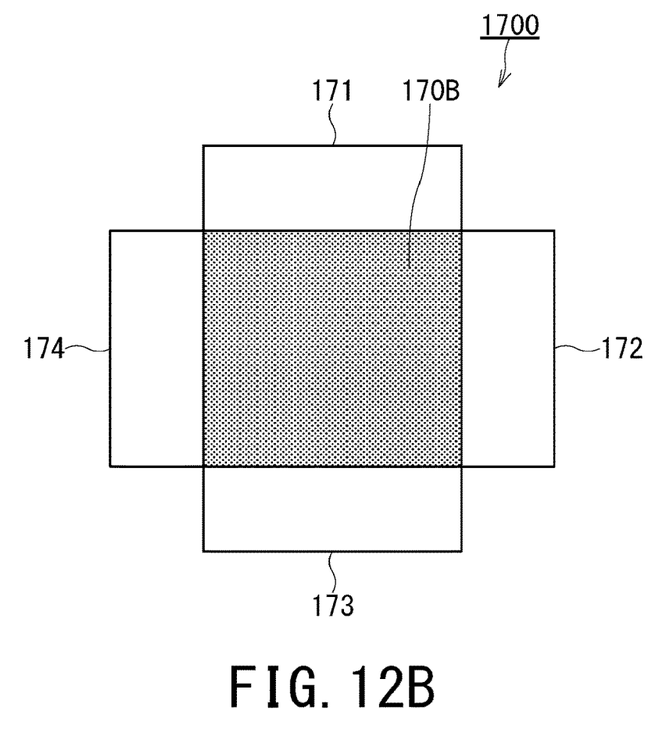

FIG. 12A and FIG. 12B are views illustrating changes in action of the four diaphragm blades 171 to 174 in the movable diaphragm 1700 of the conventional X-ray diagnostic apparatus.

In the movable diaphragm 1700 of the conventional X-ray diagnostic apparatus shown in FIG. 12A, the four diaphragm blades 171 to 174 fully close the irradiation aperture 170 to form an irradiation aperture 170A. By contrast, in the movable diaphragm 1700 of the conventional X-ray diagnostic apparatus shown in FIG. 12B, the four diaphragm blades 171 to 174 fully open the irradiation aperture 170 to form an irradiation aperture 170B.

To retract all the four diaphragm blades 171 to 174 as shown in FIG. 123, it is necessary to secure a space in the movable diaphragm 1700 for retracting the diaphragm blades 171 to 174 respectively in four directions, which raises a problem that a space for housing the diaphragm blades 171 to 174 increases.

In view of this problem, a movable diaphragm of the X-ray diagnostic apparatus according to the present embodiment forms an X-ray irradiation field, to be irradiated with X-rays by an X-ray tube, by opening/closing an irradiation aperture through which the X-rays pass, and when opening the irradiation aperture, folds and houses an X-ray shielding member, which is divided along an opening/closing direction of the irradiation aperture, on a side surface of the X-ray tube.

That is, the movable diaphragm of the X-ray diagnostic apparatus according to the embodiment houses the X-ray shielding member, which forms the irradiation aperture, along the side surface of the X-ray tube. Moreover, the movable diaphragm of the X-ray diagnostic apparatus according to the embodiment folds and houses the X-ray shielding member which forms the irradiation aperture.

Thus, the X-ray diagnostic apparatus according to the embodiment can prevent increase in the retraction space for retracting the diaphragm blades when opening the irradiation aperture, and can downsize the movable diaphragm as well as downsize the entire X-ray diagnostic apparatus.

Next, the X-ray diagnostic apparatus of the embodiment will be described with reference to the accompanying drawings.

(First Embodiment)

Figure 1:
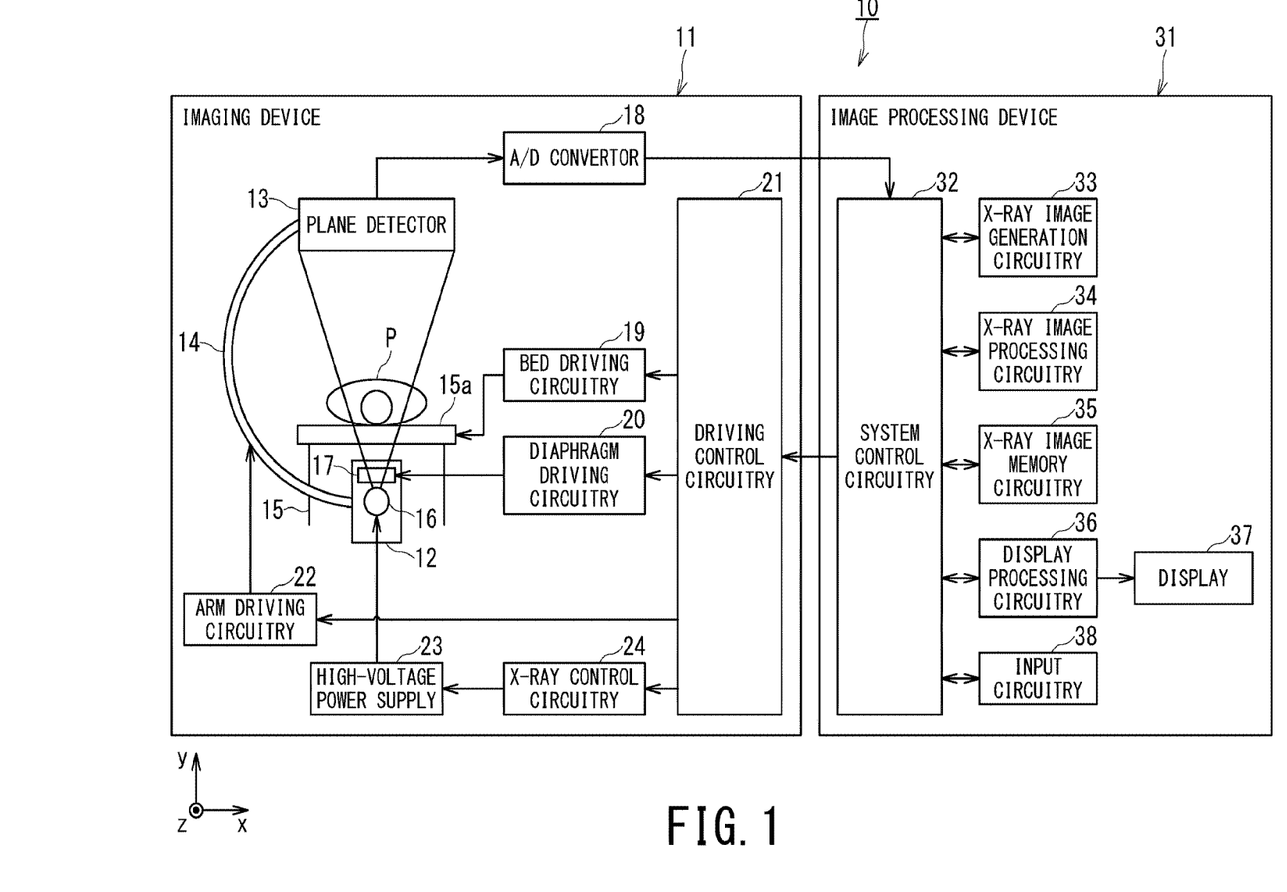
FIG. 1 is a block diagram showing a configuration of an X-ray diagnostic apparatus according to a first embodiment.

FIG. 1 is a block diagram showing a configuration of an X-ray diagnostic apparatus 10 according to a first embodiment.

As shown in FIG. 1, the X-ray diagnostic apparatus 10 according to the first embodiment is composed of an imaging device 11 and an image processing device 31.

The imaging device 11 includes an X-ray generator 12, a plane detector 13, a C-arm 14, a bed 15, a top plate 15a, an X-ray tube 16, a movable diaphragm (X-ray diaphragm) 17, an A/D (Analog to Digital) convertor 18, a bed driving circuitry 19, a diaphragm driving circuitry 20, a driving control circuitry 21, an arm driving circuitry 22, a high-voltage power supply 23, and an X-ray control circuitry 24.

The X-ray generator 12 of the imaging device 11 is provided at one end of the C-arm 14, and has the X-ray tube 16 and the movable diaphragm 17.

The X-ray tube 16 is a vacuum tube which is supplied with high-voltage power from the high-voltage power supply 23, and according to conditions of this high-voltage power, irradiates X-rays toward the plane detector 13 through an object P. At a front of the X-ray tube 16, a radiation quality adjusting filter (not shown) may be provided which adjusts quality of X-rays generated by the X-ray tube 16.

The movable diaphragm 17 forms an X-ray irradiation aperture of the X-ray tube 16, and movably supports diaphragm blades composed of an X-ray shielding material. For example, the diaphragm blades are formed from lead. As positions of the diaphragm blades are adjusted, size and shape of an X-ray irradiation field (FOV: Field of View) are adjusted. The movable diaphragm 17 is supplied with a driving signal from the diaphragm driving circuitry 20 and moves the diaphragm blades. Here, an X-ray central axis of the X-ray irradiation field is defined as a y-axis, a body axis direction of the object P orthogonal to the y-axis is defined as a z-axis, and a left-right direction of the object P orthogonal to the y-axis and the z-axis is defined as an x-axis.

In the first embodiment, the movable diaphragm 17 forms the X-ray irradiation field, to be irradiated with X-rays by the X-ray tube 16, by opening/closing the irradiation aperture through which the X-rays pass, and when opening the irradiation aperture, folds and houses an X-ray shielding member (X-ray shielding material such as lead), which is divided along an opening/closing direction of the irradiation aperture, on the side surface of the X-ray tube 16.

That is, the movable diaphragm 17 houses the X-ray shielding member, which forms the irradiation aperture, along the side surface of the X-ray tube 16. Moreover, the movable diaphragm 17 folds and houses the X-ray shielding member which forms the irradiation aperture.

The plane detector 13 has a plurality of detection elements which are two-dimensionally arrayed. Between each adjacent detection elements of the plane detector 13, a scan line and a signal line are disposed so as to intersect with each other. A grid (not shown) may be provided on a front surface of the plane detector 13. To absorb scattered radiation entering the plane detector 13 and improve contrast of X-ray images, a grid panel formed from lead etc. having high X-ray absorptivity and aluminum, a wood material, etc. having higher X-ray permeability are alternately disposed in the grid.

The C-arm 14 integrally holds the X-ray generator 12 and the plane detector 13. As the C-arm 14 is driven by the arm driving circuitry 22 under control of the driving control circuitry 21, the X-ray generator 12 and the plane detector 13 integrally move around the object P. While FIG. 1 shows an example where the C-arm 14 is an under-tube type which supports the X-ray generator 12 so as to be located under the top plate 15a, the C-arm 14 may be an over-tube type which supports the X-ray generator 12 so as to be located above the top plate 15a.

The bed 15 is installed on a floor and supports the top plate 15a. The bed 15 is controlled by the driving control circuitry 21 through the bed driving circuitry 19, and moves the top plate 15a in a horizontal direction (in-plane direction of an xz-plane) or an upper-lower direction (y-axis direction), or turns (rolls) the top plate 15a around the z-axis.

The object P is placed on the top plate 15a.

The A/D convertor 18 converts time-series projection data of an analog signals (video signal), which is output from the plane detector 13, into a digital signal and outputs it to the image processing device 31.

The driving control circuitry 21 controls driving of the bed driving circuitry 19, the diaphragm driving circuitry 20, the arm driving circuitry 22, and the X-ray control circuitry 24, during an X-ray imaging process, in accordance with control by a system control circuitry 32 of the image processing device 31.

The bed driving circuitry 19 supplies the top plate 15a with a driving signal in accordance with control by the driving control circuitry 21.

The diaphragm driving circuitry 20 supplies the movable diaphragm 17 with a driving signal in accordance with control by the driving control circuitry 21.

The high-voltage power supply 23 supplies the X-ray tube 16 with a voltage in accordance with control by the X-ray control circuitry 24.

When X-rays are generated by the X-ray tube 16 of the imaging device 11, the X-rays are irradiated at a site to be imaged of the object P. Then, the X-rays passing through the site to be imaged are detected by the plane detector 13, converted into projection data, and output to the image processing device 31.

The image processing device 31 includes the system control circuitry 32, an X-ray image generation circuitry 33, an X-ray image processing circuitry 34, an X-ray image memory circuitry 35, a display processing circuitry 36, a display 37, and an input circuitry 38.

The system control circuitry 32 of the image processing device 31 is composed of a CPU (Central Processing Unit) and a memory. Upon receiving a command which is input through an operation etc. of the input circuitry 38 by an operator, the CPU controls actions of the imaging device 11 and the entire image processing device 31.

In accordance with control by the system control circuitry 32, the X-ray image generation circuitry 33 performs a logarithmic conversion process (LOG process) on the projection data transmitted from the A/D convertor 18 of the imaging device 11, and after performing an addition process as necessary, generates an X-ray image as data. The X-ray image data generated by the X-ray image generation circuitry 33 is stored in the X-ray image memory circuitry 35.

In accordance with control by the system control circuitry 32, the X-ray image processing circuitry 34 performs an expansion/gradation/space filtering process, a minimum value/maximum value tracing process of X-ray images accumulated in time series, an addition process for removing noise, etc., on the X-ray image. The X-ray image data after the image processing by the X-ray image processing circuitry 34 is stored in the X-ray image memory circuitry 35.

The display processing circuitry 36 outputs the X-ray image generated by the X-ray image generation circuitry 33 and the X-ray image after the image processing by the X-ray image processing circuitry 34, as a video signal, to the display 37.

The display 37 displays X-ray images and infrared images output from the display processing circuitry 36 along with textual information on various parameters, a scale, etc.

The input circuitry 38 is a keyboard, a mouse, etc. which can be operated by an operator, and an input signal according to an operation is sent to the system control circuitry 32.

Next, a detailed configuration of the movable diaphragm 17 in the X-ray diagnostic apparatus 10 according to the first embodiment shown in FIG. 1 will be described.

Figure 2:
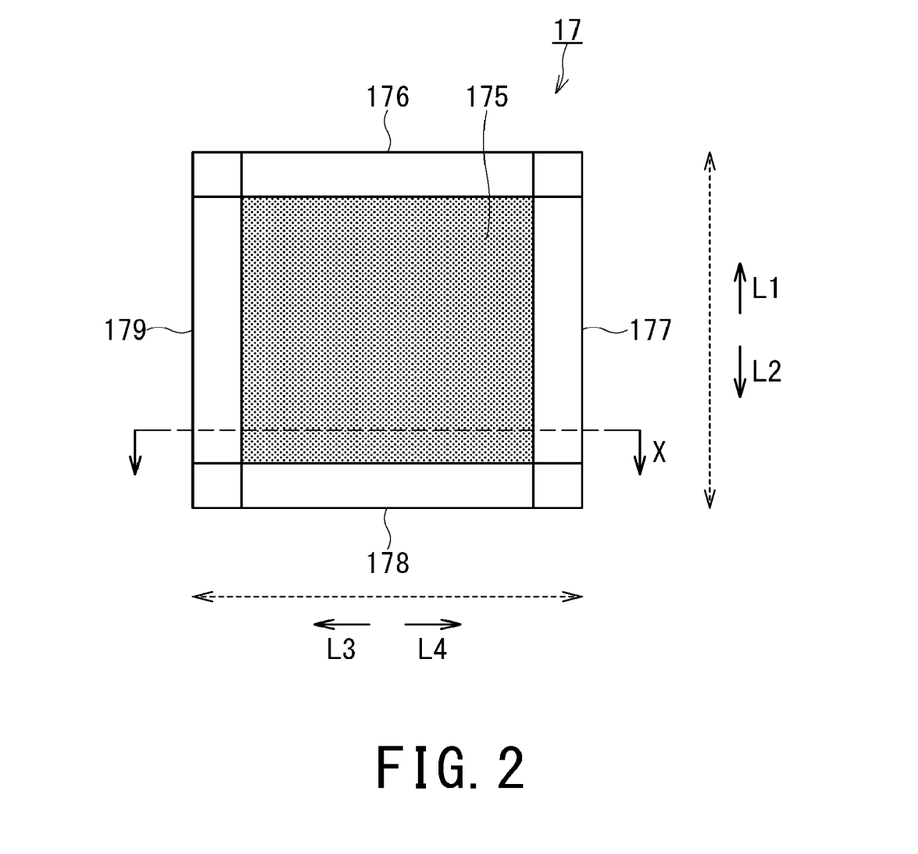
FIG. 2 is a view illustrating a configuration of a movable diaphragm in the X-ray diagnostic apparatus according to the first embodiment.

FIG. 2 is a view illustrating the configuration of the movable diaphragm 17 in the X-ray diagnostic apparatus 10 according to the first embodiment.

Similarly to the movable diaphragm 1700 provided in the conventional X-ray diagnostic apparatus, the movable diaphragm 17 of the X-ray diagnostic apparatus 10 is composed of four diaphragm blades 176 to 179 as shown in FIG. 2.

The diaphragm blade 176 and the diaphragm blade 178 make a pair and move in a direction L1 or a direction L2. The diaphragm blade 177 and the diaphragm blade 179 make a pair and move in a direction L3 or a direction L4.

The movable diaphragm 17 of the X-ray diagnostic apparatus 10 according to the first embodiment is different from the conventional X-ray diagnostic apparatus in that the former adopts a configuration where the four diaphragm blades 176 to 179 are divided in a direction along an opening/closing direction of the diaphragm blades, and when opening an irradiation aperture 175, divisions of the diaphragm blades 176 to 179 are folded and housed on the side surface of the X-ray tube 16.

Here, the configuration where the movable diaphragm 17 of the X-ray diagnostic apparatus 10 according to the first embodiment houses the four diaphragm blades 176 to 179 will be described.

Figure 3:
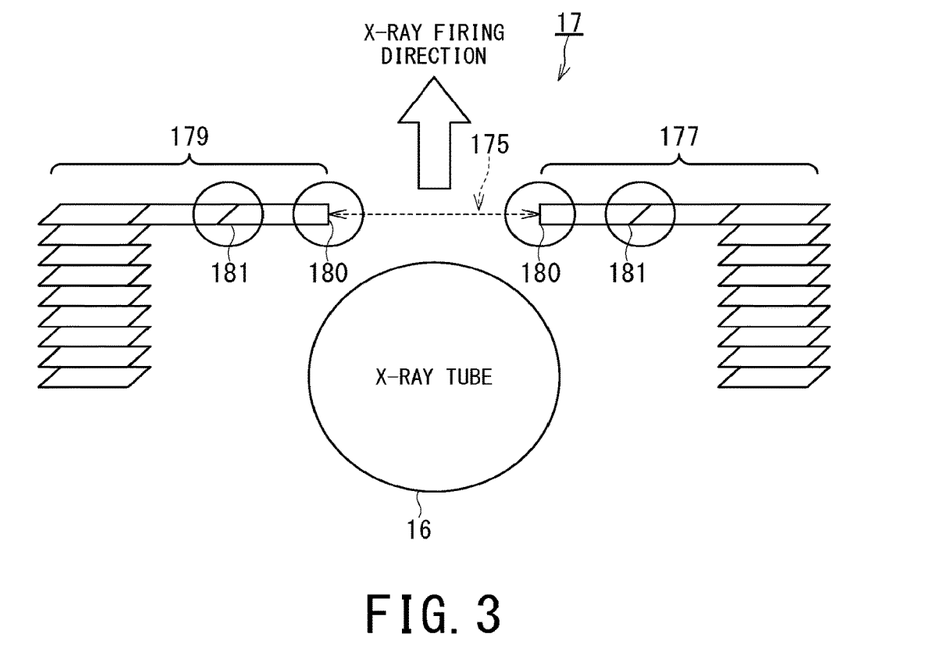
FIG. 3 is a view illustrating a cross-section in the direction X of FIG. 2, in which a part of divisions of diaphragm blades of the movable diaphragm of the X-ray diagnostic apparatus is moved.

FIG. 3 is a view illustrating a cross-section in the direction X, of FIG. 2, in which a part of divisions of the diaphragm blades 177, 179 of the movable diaphragm 17 of the X-ray diagnostic apparatus 10 is moved.

As shown in FIG. 3, when opening the irradiation aperture 175, the movable diaphragm 17 of the X-ray diagnostic apparatus 10 folds and houses the diaphragm blades (X-ray shielding members) 177, 179, which are divided in an opening/closing direction of the irradiation aperture 175, on the side surface of the X-ray tube 16. Moreover, the movable diaphragm 17 forms the X-ray irradiation field, to be irradiated with X-rays by the X-ray tube 16, by opening/closing the irradiation aperture 175, through which the X-rays pass, with the diaphragm blades 177, 179.

In the first embodiment, the divisions of the diaphragm blades 177, 179 of the movable diaphragm 17 are formed such that a section 180 on a side, on which X-rays are irradiated from the X-ray tube 16, becomes a surface perpendicular to the opening/closing direction.

Thus, the X-ray diagnostic apparatus 10 according to the first embodiment can produce effects that blurring at an end face in images taken can be prevented and that clear images can be taken.

In the divisions of the diaphragm blades 177, 179 of the movable diaphragm 17, adjacent division surfaces (sections) 181 are formed obliquely to the opening/closing direction.

Thus, the X-ray diagnostic apparatus 10 according to the first embodiment can eliminate gaps in linking portions of the diaphragm blades 177, 179, and even when a gap is created between the divisions of the diaphragm blades 177, 179, can suppress changes in thickness of the diaphragm blades 177, 179 and maintain an X-ray absorption effect (shielding effect).

The movable diaphragm 17 retracts the divisions of the diaphragm blades 177, 179 in a horizontal direction relative to the opening/closing direction of the irradiation aperture 175, and folds and houses these divisions of the diaphragm blades 177, 179 on the side surface of the X-ray tube 16. That is, the movable diaphragm 17 houses the diaphragm blades 177, 179 along the side surface of the X-ray tube 16. Moreover, the movable diaphragm 17 folds and houses the diaphragm blades 177, 179.

Thus, the X-ray diagnostic apparatus 10 according to the first embodiment can reduce a retraction space when fully opening the irradiation aperture 175 of the movable diaphragm 17 as well as can reduce a size of a main body of the movable diaphragm 17, so that the movable diaphragm 17 can be brought into close contact with the object P or the top plate 15a.

While the diaphragm blades 177, 179 have been described, the same description applies to the diaphragm blades 176, 178 as well.

While the movable diaphragm 17 houses the divisions of the diaphragm blades 177, 179 along the side surface of the X-ray tube 16, this is an example and the present invention is not limited to this example. For example, the divisions of the diaphragm blades 177, 179 may be folded and housed on a side opposite to the X-ray tube 16 across the irradiation aperture 175.

Figure 4:
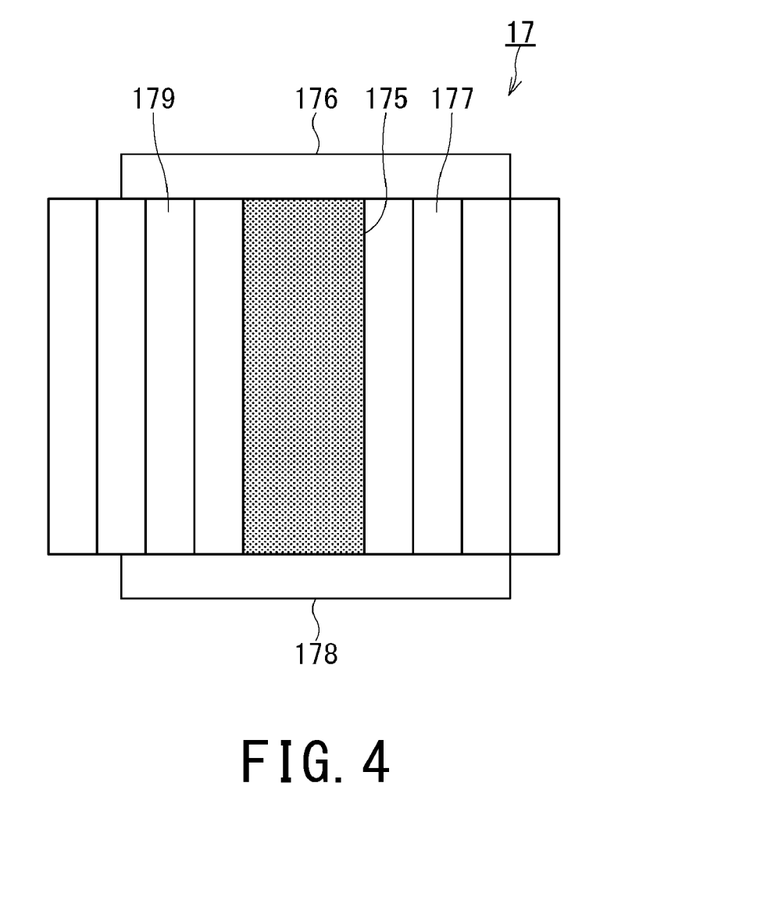
FIG. 4 is a view illustrating the diaphragm blades retracted in the movable diaphragm of the X-ray diagnostic apparatus according to the first embodiment.

FIG. 4 is a view illustrating the diaphragm blades 176 to 179 retracted in the movable diaphragm 17 of the X-ray diagnostic apparatus 10 according to the first embodiment.

In the state shown in FIG. 4, the diaphragm blades 176, 178 of the movable diaphragm 17 are retracted to fully-opened positions. On the other hand, the diaphragm blades 177, 179 of the movable diaphragm 17 each have three diaphragm blade divisions moved from retracted positions so as to partially shield the irradiation aperture 175.

While the diaphragm blades 176 to 179 are divided into predetermined sizes, a number of divisions is not particularly limited. In addition, while the state where the diaphragm blades 176, 178 are retracted to the fully-opened positions is shown, the diaphragm blades 176 to 179 of the movable diaphragm 17 can be appropriately divided into a suitable number of blade divisions so as to match a predetermined size of the movable diaphragm 17.

In the first embodiment, since the configuration where the diaphragm blades 176 to 179 of the movable diaphragm 17 are divided is adopted, the retraction space can be reduced compared with the movable diaphragm of the conventional X-ray diagnostic apparatus, so that the diaphragm blades 176 to 179 can set the irradiation aperture 175 beyond a center of the irradiation aperture 175.

Figure 5:
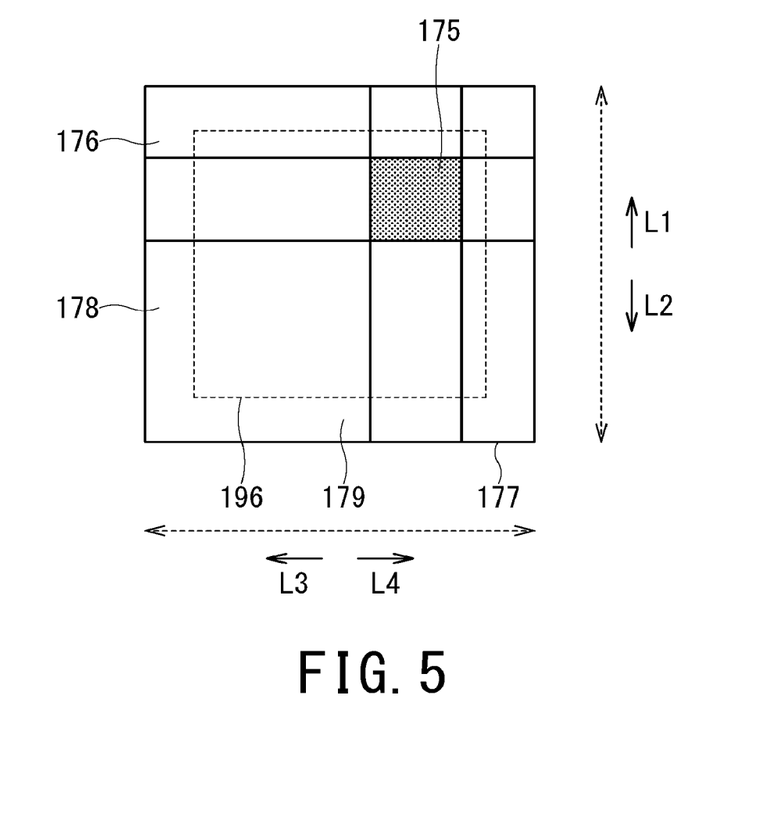
FIG. 5 is a view illustrating a state where the diaphragm blades of the movable diaphragm of the X-ray diagnostic apparatus according to the first embodiment set a center of an irradiation aperture at an arbitrary position which is different from a center of a maximum irradiation aperture indicated by the broken line.

FIG. 5 is a view illustrating a state where the diaphragm blades 178, 179 of the movable diaphragm 17 of the X-ray diagnostic apparatus 10 according to the first embodiment sets the center of the irradiation aperture 175 at an arbitrary position which is different from a center of a maximum irradiation aperture 196 indicated by the broken line.

As shown in FIG. 5, the diaphragm blade 178 of the movable diaphragm 17 sets the irradiation aperture 175 at a position beyond the center of the maximum irradiation aperture 196 in the direction L1. The diaphragm blade 179 sets the irradiation aperture 175 at a position beyond the center of the maximum irradiation aperture 196 in the direction L4.

The first embodiment having been described above is an example, and the present invention is not limited to this example. For example, the sections 181 shown in FIG. 3 may have a stepped shape.

Figure 6:
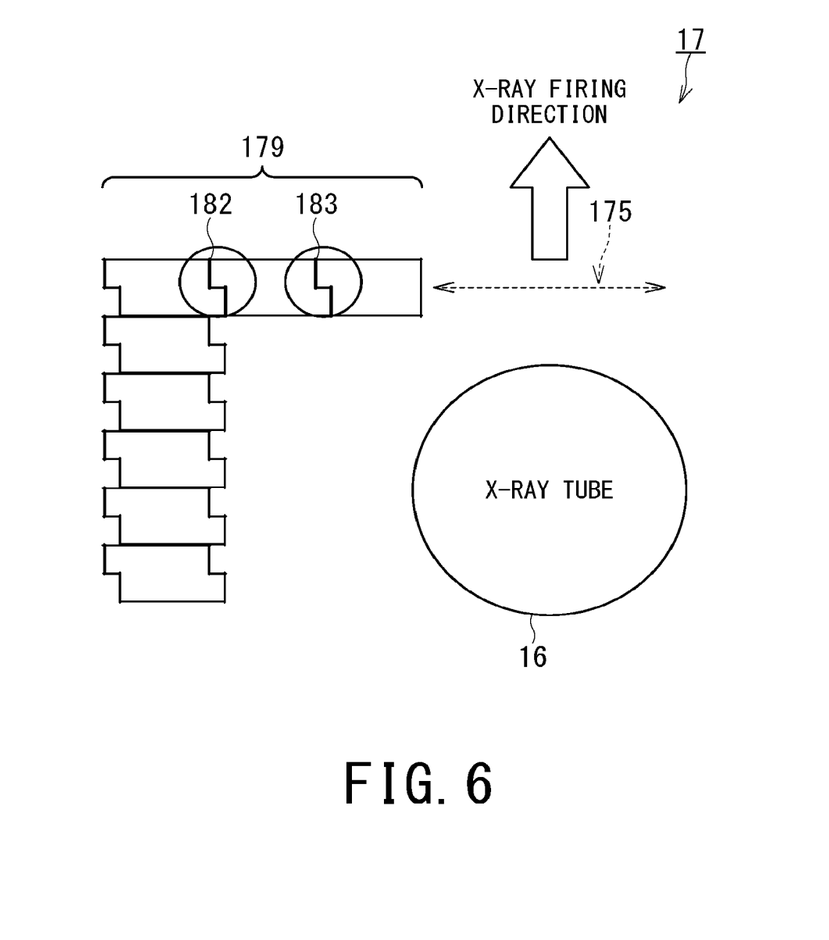
FIG. 6 is a view illustrating a configuration where a section of the diaphragm blade of the movable diaphragm of the X-ray diagnostic apparatus according to the first embodiment has a stepped shape.

FIG. 6 is a view illustrating a configuration where adjacent division sections 182, 183 of the diaphragm blade 179 of the movable diaphragm 17 of the X-ray diagnostic apparatus 10 according to the first embodiment have a stepped shape.

As shown in FIG. 6, in the diaphragm blade 179 of the movable diaphragm 17, the adjacent division sections 182, 183 of the diaphragm blade 179 have a stepped shape relative to the opening/closing direction.

Thus, for example, by forming the sections of the divisions of the diaphragm blades 176 to 179 of the movable diaphragm 17 into a stepped shape, it is possible to prevent shift of each division of the diaphragm blades, as well as to enhance transmission of a driving force when driving the divisions of the diaphragm blades.

As shown in FIG. 6, by shaping the divisions of the diaphragm blades such that a lower side (lower side in the sheet of FIG. 6) of the divisions of the diaphragm blade 179 located at a left end protrudes toward the irradiation aperture 175 (or toward the X-ray tube 16), it is possible to smoothly link or release the divisions of the diaphragm blade 179 with/from one another when housing these divisions of the diaphragm blade 179 in a longitudinal row.

Next, movement of the divisions of the diaphragm blade 179 shown in FIG. 6 will be described.

Figure 7:
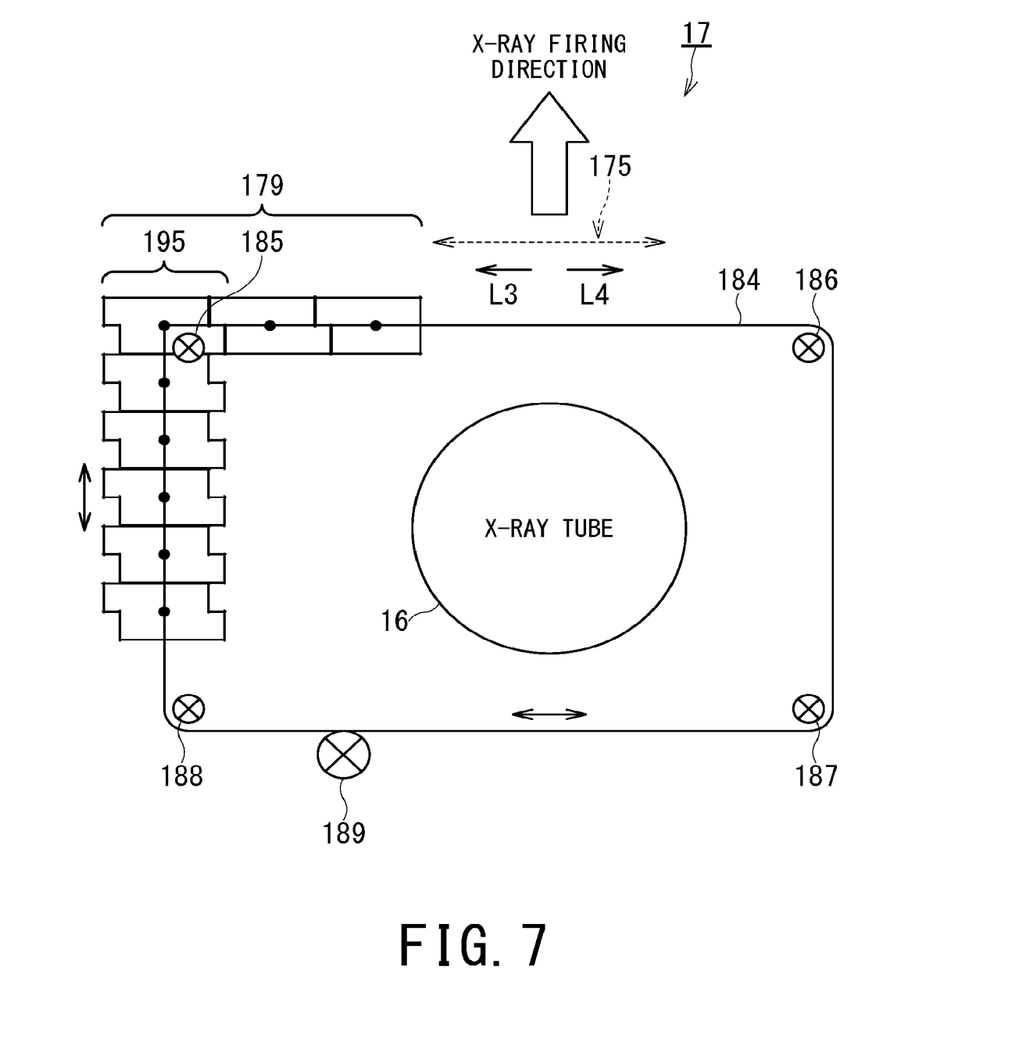
FIG. 7 is a view illustrating, relating to movement of the diaphragm blades of the movable diaphragm of the X-ray diagnostic apparatus according to the first embodiment, how to send forth or pull back diaphragm blade divisions to/from the irradiation aperture by linking these diaphragm blade divisions through a wire and pulling both ends of the wire by a motor.

FIG. 7 is a view illustrating, relating to the movement of the diaphragm blade 179 of the movable diaphragm 17 of the X-ray diagnostic apparatus 10 according to the first embodiment, how to send forth or pull back the divisions of the diaphragm blade 179 to/from the irradiation aperture 175 by linking these divisions of the diaphragm blade 179 through a wire 184 and pulling both ends of the wire 184 by a motor 189.

As shown in FIG. 7, it is possible to send forth or pull back the diaphragm blade 179 of the movable diaphragm 17 by linking the divisions of the diaphragm blade 179 through the wire 184, for example, and driving both ends of the wire 184 by the motor 189. The movable diaphragm 17 has pulleys 185 to 188 disposed at turning points of the diaphragm blade 179, and when the divisions of the diaphragm blade 179 have been moved to an end portion by the wire 184, stacks and houses the divisions of the diaphragm blade 179, for example, on the side surface of the X-ray tube 16 (the surface located on the left side of the X-ray tube 16 in the sheet of FIG. 7).

In this case, the divisions of the diaphragm blade 179, which are moved in the direction L3, are released from the linkage with the other divisions of the diaphragm blade 179 at a position of the pulley 185, and are stacked and housed in a firing direction of X-rays in a housing portion 195 where the diaphragm blade 179 is housed.

On the other hand, the divisions of the diaphragm blade 179, which are moved in the direction L4, are pulled out from the housing portion 195 at the position of the pulley 185, turn their movement direction from the direction in which the X-ray tube 16 irradiates X-rays to the direction of opening/closing the irradiation aperture 175, and are linked with the other divisions of the diaphragm blade 179 to close the irradiation aperture 175.

The pulleys 185 to 188 are an example, and alternatively the diaphragm blade 179 may be guided through a shape of the structure of the movable diaphragm 17. While the diaphragm blade 179 is moved by the wire 184 in this example, a chain may be used instead of the wire.

As has been described so far, since the X-ray diagnostic apparatus 10 according to the first embodiment can retract the diaphragm blades 176 to 179 of the movable diaphragm 17 on the side surface of the X-ray tube 16, the retraction space for the diaphragm blades 176 to 179 of the movable diaphragm 17 can be reduced as well as the size of the entire movable diaphragm 17 and the entire X-ray diagnostic apparatus 10 can be reduced.

(Second Embodiment)

In the first embodiment, the diaphragm blades 176 to 179 of the movable diaphragm 17 are housed such that the divisions of the diaphragm blades 176 to 179 are stacked in a horizontal direction relative to the opening/closing direction of the diaphragm blades 176 to 179. In the second embodiment, the diaphragm blades 176 to 179 are housed such that the divisions of the diaphragm blades 176 to 179 are stacked in a direction perpendicular to the opening/closing direction of the diaphragm blades 176 to 179.

Figure 8:
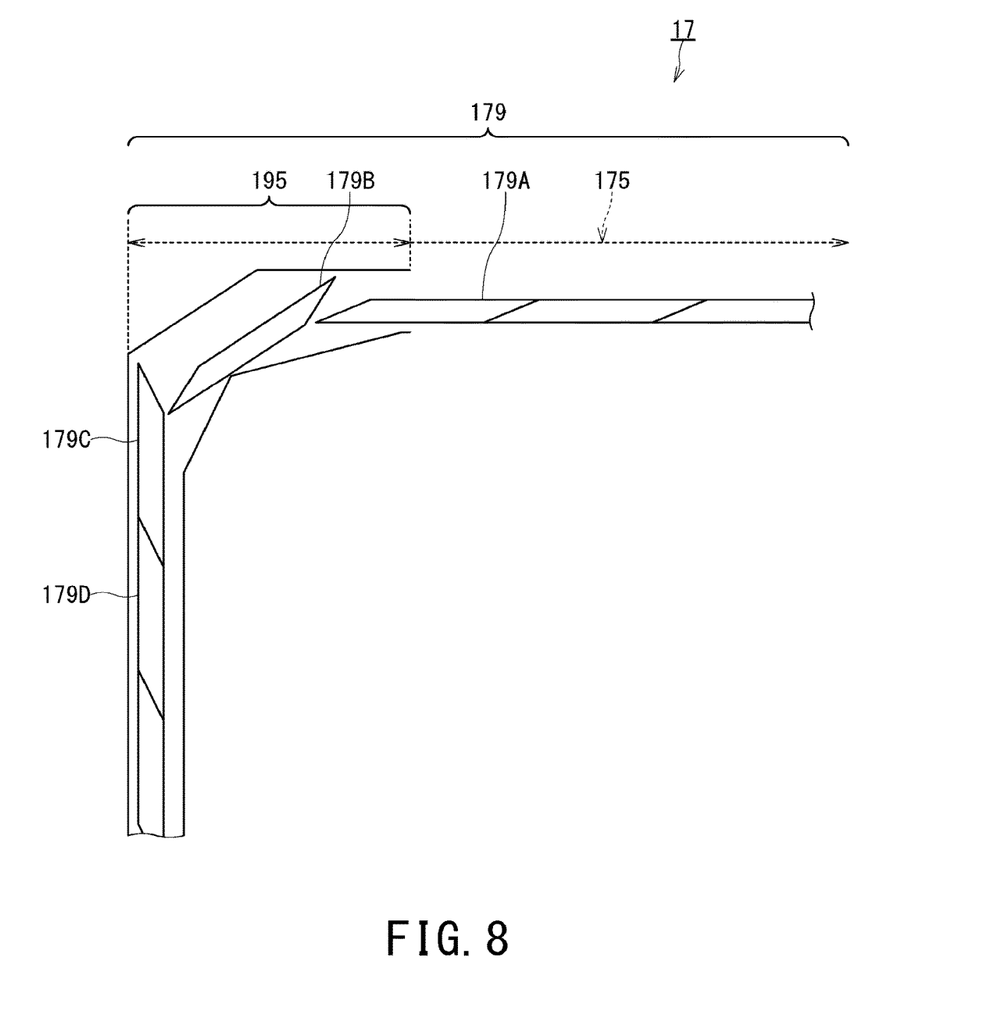
FIG. 8 is a view illustrating a state where diaphragm blade divisions of a movable diaphragm of an X-ray diagnostic apparatus according to a second embodiment are housed in a direction perpendicular to an opening/closing direction of the diaphragm blades.

FIG. 8 is a view illustrating a state where the divisions of the diaphragm blade 179 of the movable diaphragm 17 of the X-ray diagnostic apparatus 10 according to the second embodiment are housed in a direction perpendicular to the opening/closing direction of the diaphragm blade 179 (opening/closing direction of the irradiation aperture 175).

As shown in FIG. 8, in the divisions of the diaphragm blade 179 of the movable diaphragm 17 according to the second embodiment, adjacent diaphragm blade divisions are linked with each other through the wire 184 of FIG. 7, for example. A part of the divisions of the diaphragm blade 179 (e.g., diaphragm blade divisions 179C, 179D, etc.) is housed in the housing portion 195 in a direction perpendicular to the opening/closing direction of the diaphragm blade 179.

For example, the diaphragm blade 179 is divided into diaphragm blade divisions 179A to 179Z (not shown), and FIG. 8 shows a part of the diaphragm blade divisions 179A to 179D etc.

Thus, the divisions of the diaphragm blade 179 may be housed in the housing portion 195 while maintaining the linkage with the other divisions of the diaphragm blade 179.

Moreover, in the second embodiment, the divisions of the diaphragm blades 176 to 179 may be moved independently of one another.

Figure 9:
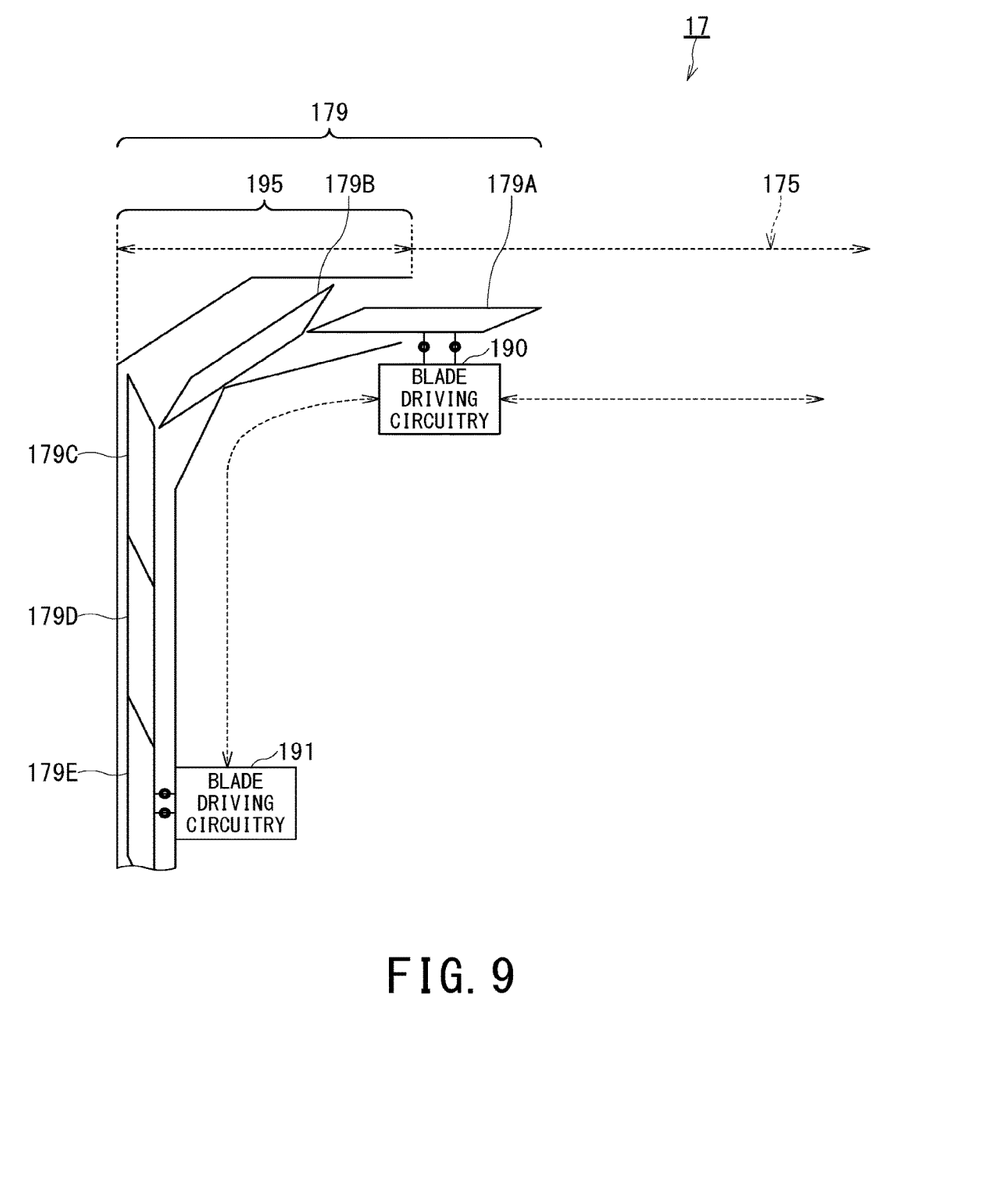
FIG. 9 is a view illustrating a structure of how the diaphragm blade divisions of the movable diaphragm of the X-ray diagnostic apparatus according to the second embodiment move as single bodies.

FIG. 9 is a view illustrating a structure of how the divisions of the diaphragm blade 179 of the movable diaphragm 17 of the X-ray diagnostic apparatus 10 according to the second embodiment move as single bodies.

As shown in FIG. 9, the diaphragm blade 179 is divided, for example, into the diaphragm blade divisions 179A to 179E, and FIG. 9 shows a case where the diaphragm blade division 179A is provided with a blade driving circuitry 190 and a case where the diaphragm blade division 179E is provided with a blade driving circuitry 191.

The blade driving circuitries 190, 191 constitute a driving circuitry which allows the diaphragm blade divisions 179A to 179E to move as single bodies. The blade driving circuitries 190, 191 connect with a diaphragm blade division, which is to be moved as a single body, out of the diaphragm blade divisions 179A to 179E, and move integrally with that diaphragm blade division.

The blade driving circuitries 190, 191 can also drive a plurality of divisions of the diaphragm blade 179. For example, to open the irradiation aperture 175, the blade driving circuitry 190 connects with the diaphragm blade division 179A and drives such that the other diaphragm blade divisions 1796 to 179E are pushed out from the irradiation aperture 175 to the housing portion 195.

In this case, since the diaphragm blade division 179A pushes out the diaphragm blade divisions 179B to 179E, the blade driving circuitry 190 can move the diaphragm blade divisions 179A to 179E toward the housing portion 195 and open the irradiation aperture 175. The blade driving circuitry 190 can move the diaphragm blade divisions 179A to 179E to predetermined positions according to a desired size of the irradiation aperture 175, and house a part of the diaphragm blade divisions 179A to 179E in the housing portion 195.

To close the irradiation aperture 175, the blade driving circuitry 191 connects with the diaphragm blade division 179E and drives such that the other diaphragm blade divisions 179A to 179D are pushed out from the housing portion 195 to the irradiation aperture 175.

In this case, since the diaphragm blade division 179E pushes out the diaphragm blade divisions 179A to 179D, the blade driving circuitry 191 can move the diaphragm blade divisions 179A to 179E toward the irradiation aperture 175 to shield the irradiation aperture 175.

The blade driving circuitries 190, 191 can connect with any of the diaphragm blade divisions 179A to 179E, and have same functions. There may be only either the blade driving circuitry 190 or the blade driving circuitry 191, or two or more blade driving circuitries.

Figure 10A:
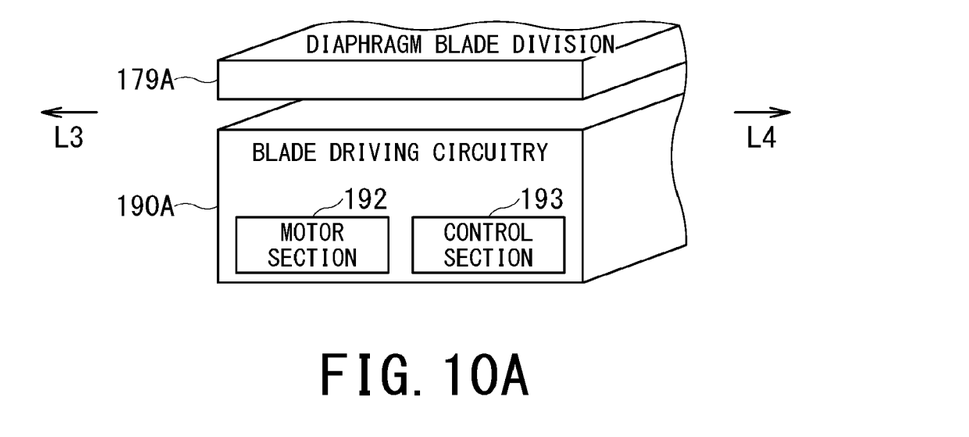
FIG. 10A and FIG. 10B are views illustrating structures of how a diaphragm blade division of the movable diaphragm of the X-ray diagnostic apparatus according to the second embodiment connects with a blade driving circuitry.
Figure 10B:
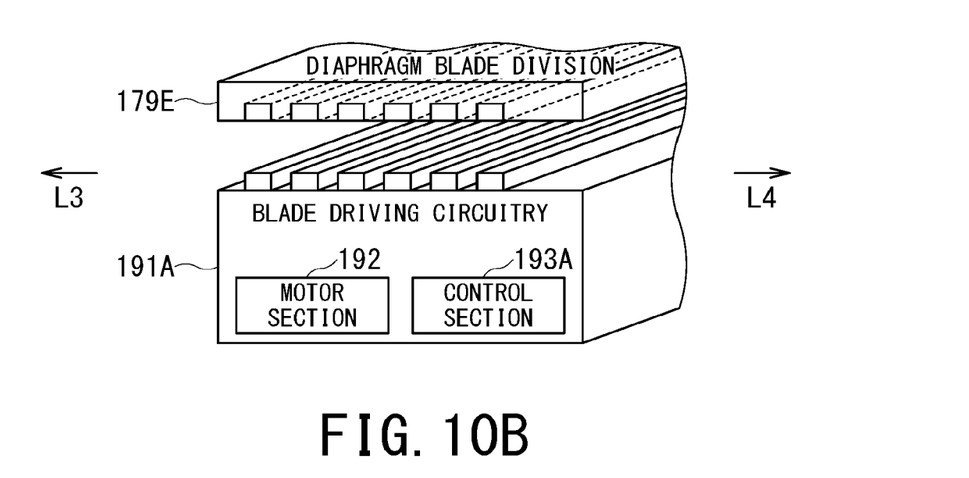

FIG. 10A and FIG. 10B are views illustrating structures of how the diaphragm blade divisions 179A, 179E of the movable diaphragm 17 of the X-ray diagnostic apparatus 10 according to the second embodiment connect with the blade driving circuitries 190, 191.

As shown in FIG. 10A, for example, a blade driving circuitry 190A includes a motor section 192 and a control section 193. The control section 193 includes an electromagnet, and the diaphragm blade division 179A includes a metal such as iron or nickel which is attracted to the electromagnet.

The blade driving circuitry 190A generates a magnetic force, while controlling a current by the control section 193, to connect the electromagnet and the diaphragm blade division 179A with each other. In a state where the diaphragm blade division 179A and the blade driving circuitry 190A are connected with each other, the motor section 192 movably drives the diaphragm blade division 179A, for example, from the housing portion 195 (see FIG. 9) to the irradiation aperture 175.

While the blade driving circuitry 190A is moving the diaphragm blade division 179A, the control section 193 keeps generating a magnetic force and the blade driving circuitry 190A and the diaphragm blade division 179A move in a connected state. On the other hand, to move the blade driving circuitry 190A as a single body or to release the blade driving circuitry 190A from the connection with the diaphragm blade division 179A, the control section 193 turns off current and removes the magnetic force of the electromagnet.

While the blade driving circuitry 190A includes the motor section 192 and the control section 193, it is not necessary that the blade driving circuitry 190A is integral with these sections, and the blade driving circuitry 190A may be provided with a magnetic force and a driving force by a motor section 192 and a control section 193 which are separately provided.

As shown in FIG. 10B, for example, a blade driving circuitry 191A also includes the motor section 192 and a control section 193A.

The blade driving circuitry 191A and the diaphragm blade division 179E shown in FIG. 10B are different from the blade driving circuitry 190A and the diaphragm blade division 179A shown in FIG. 10A in that the diaphragm blade division 179E and the blade driving circuitry 191A are provided with notches formed by concave portions and convex portions.

The control section 193A of the blade driving circuitry 191A includes a solenoid, for example, and can move up and down the convex portions provided in the blade driving circuitry 191A by controlling turning on/off of the solenoid. Except for these convex portions and concave portions, the configuration of the blade driving circuitry 191A and the diaphragm blade division 179E is the same as the configuration of the blade driving circuitry 190A and the diaphragm blade division 179A shown in FIG. 10A.

For example, as the control section 193A turns on the solenoid and moves upward the convex portions of the blade driving circuitry 191A, the blade driving circuitry 191A can connect its convex portions with the concave portions of the diaphragm blade division 179E to connect with the diaphragm blade 179E.

As the control section 193A turns off the solenoid and moves the convex portions of the blade driving circuitry 191A downward, the blade driving circuitry 191A can separate its convex portions from the concave portions of the diaphragm blade division 179E to separate itself from the diaphragm blade division 179E.

Next, two methods for fixing the divisions of the diaphragm blade 179 at a predetermined position of the irradiation aperture 175 will be described.

In a first fixing method, for example, a guide member (not shown) which guides the movement of the divisions of the diaphragm blade 179 is provided with a plurality of convex portions, and these convex portions constitute a fixing portion.

In this case, the divisions of the diaphragm blade 179 are provided with the concave portions shown in FIG. 10B and the configuration of the diaphragm blade division 179E is adopted. Accordingly, the convex portions of the guide member provided as the fixing portion and the concave portions of the diaphragm blade 179 fit with one another, and the divisions of the diaphragm blade 179 can be fixed on the guide member.

In the first fixing method, first, the control section 193A of the blade driving circuitry 191A turns on the solenoid, and thereby the blade driving circuitry 191A moves the convex portions of the blade driving circuitry 191A upward. This causes the diaphragm blade division 179E to be pushed upward. As a result, the diaphragm blade division 179E is disengaged and released from the convex portions of the guide member.

Next, with the convex portions of the blade driving circuitry 191A and the concave portions of the diaphragm blade division 179E connected, the released diaphragm blade division 179E is moved to a predetermined desired position of fixing by driving of the blade driving circuitry 191A and stops at that position. Then, at the stop position, as the control section 193A of the blade driving circuitry 191A turns off the solenoid, the blade driving circuitry 191A moves the convex portions of the blade driving circuitry 191A downward. As a result, the stopped diaphragm blade division 179E is disengaged and released from the blade driving circuitry 191A.

Then, the diaphragm blade division 179E released from the blade driving circuitry 191A moves downward to the fixing portion of the guide member, and as the convex portions of the fixing portion of the guide member and the concave portions of the diaphragm blade division 179E fit with one another at the stop position, the diaphragm blade division 179E is fixed at that position.

In a second fixing method, for example, a guide member which guides the movement of the divisions of the diaphragm blade 179 is provided with an electromagnet, a current is applied to a position at which the diaphragm blade 179 is to be fixed, and a magnetic force of the electromagnet constitutes a fixing portion.

In this case, the divisions of the diaphragm blade 179 include a metal such as iron or nickel which is attracted to the electromagnet, and the configuration of the diaphragm blade division 179A is adopted. Accordingly, the divisions of the diaphragm blade 179 can be fixed by the electromagnet, which is provided as the fixing portion of the guide member, and the metal of the diaphragm blade division 179A.

In the second fixing method, the divisions of the diaphragm blade 179 is moved to a predetermined desired position of fixing by the blade driving circuitry 190 etc., and at the stop position, as the control section 193 of the blade driving circuitry 190 turns off current, the diaphragm blade 179 is released from the blade driving circuitry 190. As a current is applied to the electromagnet of the guide member and a magnetic force is generated in the electromagnet of the guide member, the released diaphragm blade 179 is fixed at the position by the magnetic force and the metal of the diaphragm blade 179.

As has been described above, in the second embodiment, since the divisions of the diaphragm blades 176 to 179 can be moved as single bodies and independently of one another, a predetermined part of the irradiation aperture 175 can be shielded.

Thus, the divided diaphragm blades 176 to 179 of the movable diaphragm 17 of the X-ray diagnostic apparatus 10 according to the second embodiment can be used as an antihalation filter between legs, for example, in lower extremity vascular testing.

It is also possible to adjust an extent of X-ray shielding through an overlap by adopting a configuration which allows the divisions of the diaphragm blade 179 to move as single bodies, and a configuration which allows, for example, some of the diaphragm blade divisions 179A to 179E to overlap one another.

For example, if the diaphragm blade divisions 179A to 179E are overlapped obliquely, a portion where an amount of overlap is small becomes thinner, and a thickness of the filter can be adjusted.

In the first embodiment and the second embodiment, since the diaphragm blades 176 to 179 of the movable diaphragm 17 are housed on the side surface of the X-ray tube 16, leakage of X-rays irradiated by the X-ray tube 16 can also be prevented.

In the second embodiment, since the diaphragm blades 176 to 179 can be fixed on the movable diaphragm 17, even when the C-arm 14 is turned for imaging and the movable diaphragm 17 of the X-ray diagnostic apparatus 10 is tilted, the diaphragm blades 176 to 179 can maintain a stable state without rattling. Thus, in the second embodiment, influences of the turning C-arm 14 etc. can be prevented.

While some embodiments of the present invention have been described, these embodiments have been presented as examples and are not intended to limit the scope of the invention. These novel embodiments can be implemented in various other forms, and various omissions, substitutions, and changes can be made within the scope of the invention. These embodiments and their modifications are included in the scope and gist of the present invention, as well as in the invention described in the scope of claims and an equivalent scope.

What is claimed is:

1. An X-ray diagnostic apparatus, comprising:
    an X-ray tube configured to generate X-rays to be irradiated at an object;
    an X-ray diaphragm configured to house X-ray shielding members forming an irradiation aperture, through which the X-rays pass, along a side surface of the X-ray tube;
    an X-ray detector configured to detect X-rays passing through the object; and
    image data generation circuitry configured to generate image data based on X-rays detected by the X-ray detector, wherein
    the irradiation aperture is formed by opening/closing the X-ray shielding members,
    the X-ray shielding members include at least one pair of X-ray shielding members, the X-ray shielding members constituting the at least one pair of X-ray shielding members being disposed opposite the irradiation aperture to each other, and
    each of the X-ray shielding members constituting the at least one pair of X-ray shielding members is divided along a direction of opening/closing the irradiation aperture into a plurality of divisions.

2. An X-ray diagnostic apparatus, comprising:
an X-ray tube configured to generate X-rays to be irradiated at an object;
an X-ray diaphragm configured to fold and house X-ray shielding members forming an irradiation aperture through which the X-rays pass;
an X-ray detector configured to detect X-rays passing through the object; and
image data generation circuitry configured to generate image data based on X-rays detected by the X-ray detector, wherein
the irradiation aperture is formed by opening/closing the X-ray shielding members,
the X-ray shielding members include at least one pair of X-ray shielding members, the X-ray shielding members constituting the at least one pair of X-ray shielding members being disposed opposite the irradiation operation to each other, and
each of the X-ray shielding members constituting the at least one pair of X-ray shielding members is divided along a direction of opening/closing the irradiation aperture into a plurality of divisions.

3. The X-ray diagnostic apparatus according to claim 1, wherein the X-ray diaphragm retracts the divisions of each X-ray shielding member in a horizontal direction relative to a direction of opening/closing the irradiation aperture, and folds and houses the divisions of each X-ray shielding member on the side surface of the X-ray tube.

4. The X-ray diagnostic apparatus according to claim 2, wherein the X-ray diaphragm retracts the divisions of each X-ray shielding member in a horizontal direction relative to a direction of opening/closing the irradiation aperture, and folds and houses the divisions of each X-ray shielding member on the side surface of the X-ray tube.

5. The X-ray diagnostic apparatus according to claim 1, wherein the X-ray diaphragm retracts the divisions of each X-ray shielding member in a horizontal direction relative to a direction of opening/closing the irradiation aperture, and houses the divisions of each X-ray shielding member in a direction perpendicular to the direction of opening/closing the irradiation aperture.

6. The X-ray diagnostic apparatus according to claim 2, wherein the X-ray diaphragm retracts the divisions of each X-ray shielding member in a horizontal direction relative to a direction of opening/closing the irradiation aperture, and houses the divisions of each X-ray shielding member in a direction perpendicular to the direction of opening/closing the irradiation aperture.

7. The X-ray diagnostic apparatus according to claim 1, wherein adjacent surfaces of the divisions of each X-ray shielding member of the X-ray diaphragm are formed obliquely to an opening/closing direction of the irradiation aperture.

8. The X-ray diagnostic apparatus according to claim 2, wherein adjacent surfaces of the divisions of each X-ray shielding member of the X-ray diaphragm are formed obliquely to an opening/closing direction of the irradiation aperture.

9. The X-ray diagnostic apparatus according to claim 1, wherein adjacent surfaces of the divisions of each X-ray shielding member of the X-ray diaphragm are formed in a stepped shape.

10. The X-ray diagnostic apparatus according to claim 2, wherein adjacent surfaces of the divisions of each X-ray shielding member of the X-ray diaphragm are formed in a stepped shape.

11. The X-ray diagnostic apparatus according to claim 1, wherein a section of each X-ray shielding member of the X-ray diaphragm located on a side on which the X-rays are irradiated is formed as a surface perpendicular to a direction of opening/closing the irradiation aperture.

12. The X-ray diagnostic apparatus according to claim 2, wherein a section of each X-ray shielding member of the X-ray diaphragm located on a side on which the X-rays are irradiated is formed as a surface perpendicular to a direction of opening/closing the irradiation aperture.

13. The X-ray diagnostic apparatus according to claim 1, wherein
the X-ray diaphragm includes driving circuitry configured to drive the divisions of each X-ray shielding member, and
the driving circuitry drives the divisions of each X-ray shielding member as single bodies and shields a part of the irradiation aperture by the divisions of each X-ray shielding member.

14. The X-ray diagnostic apparatus according to claim 2, wherein
the X-ray diaphragm includes a driving circuitry configured to drive the divisions of the X-ray shielding members, and
the driving circuitry drives the divisions of each X-ray shielding member as single bodies and shields a part of the irradiation aperture by the divisions of each X-ray shielding member.

15. An X-ray diaphragm which forms an X-ray irradiation field, to be irradiated with X-rays, by opening/closing an irradiation aperture through which the X-rays pass, the X-ray diaphragm comprising X-ray shielding members, wherein
the X-ray shielding members include at least one pair of X-ray shielding members, the X-ray shielding members constituting the at least one pair of X-ray shielding members being disposed opposite the irradiation aperture to each other,
each of the X-ray shielding members constituting the at least one pair of X-ray shielding members is divided along a direction of opening/closing the irradiation aperture into a plurality of divisions, and
when the irradiation aperture is opened, the divisions of the X-ray shielding members are housed along a side surface along which the X-rays are irradiated.

* * * * *